(12) United States Patent
Wennogle et al.

(10) Patent No.: US 8,183,266 B2
(45) Date of Patent: May 22, 2012

(54) METHODS

(75) Inventors: Lawrence P. Wennogle, New York, NY (US); Peng Li, New York, NY (US); Jun Zhao, New York, NY (US)

(73) Assignee: Intra-Cellular Therapies, Inc., New York, NY (US)

( * ) Notice: Subject to any disclaimer, the term of this patent is extended or adjusted under 35 U.S.C. 154(b) by 350 days.

(21) Appl. No.: 12/663,114

(22) PCT Filed: Jun. 4, 2008

(86) PCT No.: PCT/US2008/007011
§ 371 (c)(1),
(2), (4) Date: Dec. 4, 2009

(87) PCT Pub. No.: WO2008/150528
PCT Pub. Date: Dec. 11, 2008

(65) Prior Publication Data
US 2010/0173951 A1   Jul. 8, 2010

Related U.S. Application Data

(60) Provisional application No. 60/933,037, filed on Jun. 4, 2007, provisional application No. 61/033,720, filed on Mar. 4, 2008.

(51) Int. Cl.
A61K 31/44      (2006.01)
A61K 31/4406    (2006.01)
C07D 213/69     (2006.01)
C07D 213/68     (2006.01)
C07D 213/61     (2006.01)
A61P 25/22      (2006.01)

(52) U.S. Cl. ........ 514/348; 514/349; 514/351; 546/296; 546/297; 546/300

(58) Field of Classification Search .................. None
See application file for complete search history.

(56) References Cited

U.S. PATENT DOCUMENTS

| | | |
|---|---|---|
| 4,296,126 A | 10/1981 | Nedelec et al. |
| 5,166,437 A | 11/1992 | Kairisalo et al. |
| 2004/0242554 A1 | 12/2004 | Nilsson et al. |
| 2005/0004398 A1 | 1/2005 | Fernandez et al. |

FOREIGN PATENT DOCUMENTS

GB   2060622   5/1981

OTHER PUBLICATIONS

Lakshmi, E., et al., "(R)-N-Methyl-3-(3-$^{125}$I-pyridin-2-yloxy)-3-phenylpropan-1-amine: a novel probe for norepinephrine transporters", *Nuclear Medicine and Biology*, Elsevier, NY, US, vol. 35, No. 1, pp. 43-52, (2007).

*Primary Examiner* — Kamal Saeed
(74) *Attorney, Agent, or Firm* — Hoxie & Associates, LLC

(57) ABSTRACT

The invention relates to the novel chemical compounds of the formula (I): (I) in free or salt form, its use in the treatment of NET and/or SERT mediated conditions, e.g., depression, vasomotor symptoms, e.g., hot flashes and other diseases or conditions mediated by NET and/or SERT.

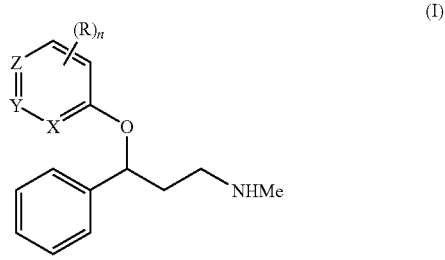

(I)

17 Claims, No Drawings

METHODS

This application claims priority from U.S. Provisional Application No. 60/933,037, filed Jun. 4, 2007, and U.S. Provisional Application No. 61/033,720, filed Mar. 4, 2008, the contents of both of which are hereby incorporated by reference in their entirety.

FIELD OF THE INVENTION

The present invention relates to novel N-methyl pyridinoxy phenylpropanamines, their pharmaceutical compositions and methods of use. In particular, the present invention relates to (R)-(−)-N-methyl-3-substituted pyridinoxy-3-phenylpropanamines and their use. In addition, the present invention relates to therapeutic methods that penetrate the blood-brain barrier and regulate the norepinephrine and serotonin transporters ("NET/SERT"). Accordingly, the compounds and compositions of the present invention are useful in the treatment of depression, vasomotor symptoms, e.g., hot flashes and other diseases or conditions mediated by norepinephrine transporters ("NET") and/or serotonin transporters ("SERT").

BACKGROUND OF THE INVENTION

Without being bound to theory, it is believed that NET, a 12 membrane spanning protein, located presynaptically on noradrenergic nerve terminals, plays a critical role in the regulation of the synaptic norepinephrine ("NE") concentration via the reuptake of NE (R. D. Blakely et al., *J. Exp. Biol.*, 196: 263-281 (1994); T. Pacholczyk et al., *Nature*, 350:350-354 (1994); and S. G. Amara et al., *Annu. Rev. Neurosci.*, 16:73-93 (1993)). The NET is critical for the removal of NE from the extracellular space (J. Axelrod et al., *Porg. Brain Res.*, 31:21-32 (1969); H. Bonisch at al., *Ann. N.Y. Acad. Sci.*, 733:193-202 (1994)) and is a target for antidepressant drug actions (J. C. Nelso, *Psychiatry*, 46:1301-1308 (1999) and H. J. Moller, *J. Clin. Psychiatry*, 61(Supp. 6):24-27 (2000)).

Many antidepressant drugs act by binding serotonin transporters ("SERT") and/or NET to increase serotonin and norepinephrine levels at neuronal synapses. While the role of SERTs in depression has long been explored, the NE system has only recently been proposed to be important in the treatment of depression. In the past, tricyclic antidepressant ("TCA") compounds and monoamine oxidase inhibitors ("MAOI") represented the major pharmacological treatments for this illness. Such drugs have the disadvantage of their low selectivity and interaction with several other types of receptors causing unwanted side effects (A. J. Frazer, *J. Clin. Psychiatry*, 58(Supp. 6):9-25 (1997)).

In an attempt to provide improved medications, selective serotonin reuptake inhibitors ("SSRI") such as fluoxetine, nisoxetine, reboxetine, and their analogues (shown below) have been developed to treat depression.

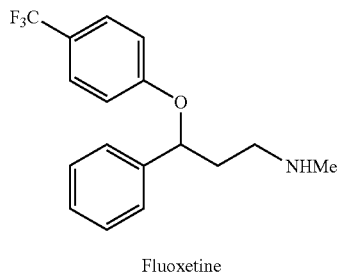

Fluoxetine

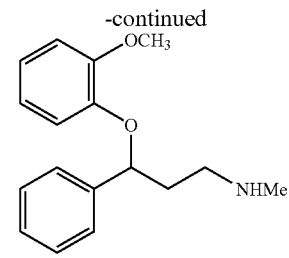

Nisoxetine

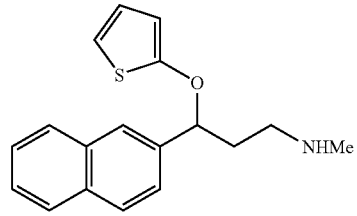

Duloxetine

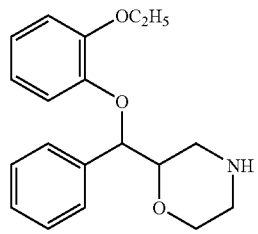 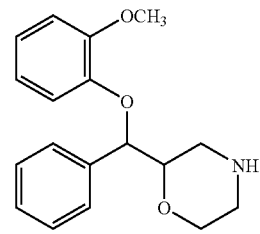

Reboxetine                    MeNER

Some of these compounds are quite effective in certain patient populations. However, their use is often limited by side effects, particularly those thought to be mediated by their anticholinergic properties (R. Valentino et al., *Ann. N.Y. Acad. Sci.*, 697:171-187 (1993); R. Mongeau et al., *Brain Res. Rev.*, 23:145-195 (1997)). No simple increase or decrease in neuronal activity is likely to be the primary cause of depression. It may be that a complex dysregulation of the Locus Coeruleus-Norepinephrine system may play an important role in depression (K. J. Ressler et al., *Biol. Psychiatry*, 46:1219-1233 (1999)). Different studies had significant differences in NE metabolites and changes in receptor populations (D. Charney, *J. Clin. Psychiatry*, 59:11-14 (1998); B. Leonard, *J. Psychopharmacol.*, 11:s39-s47 (1997); A. Schatzberg et al., "*Psychopharmacology: The Fourth Generation of Progress*", pp. 911-920 (1995)).

In addition to depression, the role of NET has also recently been implicated in thermoregulatory dysfunctions such as vasomotor symptoms, e.g., hot flashes experienced by naturally, chemically or surgically induced menopausal women. Although the physiology of hot flashes is still poorly understood today, studies have revealed an association of increased levels of norepinephrine in the preoptic hypothalamus in the brain to hot flashes. There is also supportive evidence for the role of norepinephrine (NE) and serotonin (5-HT) in thermoregulation. Compounds that modulate norepinephrine levels are therefore useful for the treatment of vasomotor symptoms.

The availability of new imaging tools such as selective positron emission tomography ("PET") and/or single photon emission computed tomography ("SPECT") radioligands for mapping specific transporter systems have significantly advanced the understanding of the field of depression and will be similarly useful in the understanding of other NET/SERT mediated disorders such as dysphoria, anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, fibromyalgia, and vasomotor symptoms, e.g., hot flashes, especially anxiety and depression. PET and SPECT make possible the direct study and quantification of neurotransmitter systems in the human brain and better understand psychiatric diseases. These target-specific radiotracers facilitate the development of therapeutic agents for depressive illness, optimize the therapeutic dosage, and monitor the efficacy of treatment. Despite recognition of the high importance of the NET as a site of action of many old (e.g. desipramine) and new (e.g. reboxetine) antidepressant drugs in the brain, and even though the NET has long been recognized in relation to the pathophysiology and treatment of ADHD, substance abuse, and depression, there have been relatively few attempts to develop radiotracers for imaging NET in vivo in the central nervous system ("CNS"), either by PET or SPECT (Wilson et al., *Nuclear Medicine and Biology*, 30:85-92 (2003)).

Hake et al., *Nucl. Med. Biol.*, 16:771-774 (1989) reported the synthesis of [$^{11}$C]nisoxetine which demonstrated only modest specific binding in mice. Kung et al., *Eur. J. Nucl. Med. Molecular Imaging*, 26:844-853 (1999) synthesized an iodinated derivative of tomoxetine that showed a low degree of saturable binding in vivo in rat brain, and very high lung uptake. Chumpradit et al., *J. Med. Chem.*, 35:4492-4497 (1992) and Koch et al., *Neuropeychopharmacology* 27:949-959 (2002) demonstrated in vitro that (R)-derivatives of fluoxetine had higher affinity to NE uptake sites than corresponding (S)-derivatives. Stolin et al., *Chirality*, 7:285-289 (1995) showed that the (S,S) enantiomer of reboxetine is more potent than its (R,R) enantiomer ($IC_{50}$3.6 nM and 85 nM respectively) in inhibiting the NE uptake in rat hypothalamic synaptosomes. Ding et al., *Synapse* 50:345-352 (2003) reported an evaluation of the individual enantiomers of reboxetine methyl analog [$^{11}$C]MRB as radioligands for PET imaging studies of NET systems in baboons, both in brain and in peripheral organs. However, the results were not optimal due to high non-specific biding in vivo. The MRB tracer also displayed unexpected high uptake in striatum, a region that contains low levels of NET, and some binding to sites other than NET is suspected. Van Dort et al., *Nuclear Medicine and Biology*, 24:707-711 (1997) has reported the radiosysnthesis of [$^{11}$C]desipramine but no in vivo data have been published yet.

There remains a need for a NET/SERT ligand with moderate lipophilicity and high binding affinity. Although the affinity of nisoxetine for NET is high, its lipophilicity is also undesirably high at log P>3.5.

SUMMARY OF THE INVENTION

The present invention is directed to compounds of formula (I) and their use as NET/SERT modulators, e.g., NET/SERT inhibitors:

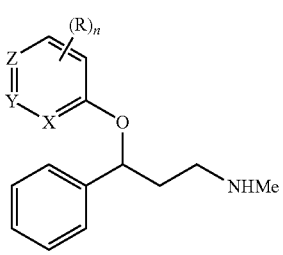

in free or salt form, e.g., for the treatment of depression (including major depressive disorder, dysthymia, adjustment disorder with depressed mood, and depression associated with bipolar disorder), dysphoria, anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, fibromyalgia, and naturally, surgically or medically-induced menopausal or andropausal symptoms such as vasomotor symptoms, e.g., hot flashes. Compounds of Formula (I) are especially useful for the treatment of anxiety, depression and vasomotor symptoms, e.g., hot flashes.

DETAILED DESCRIPTION OF THE INVENTION

The compounds of the present invention are represented by formula (I):

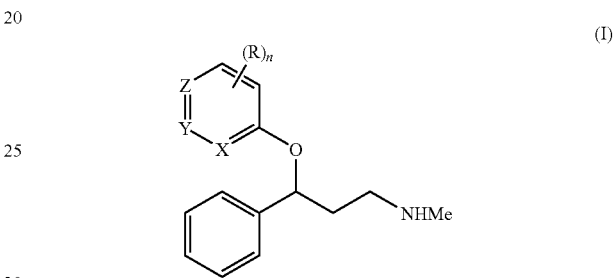

in free or salt form, wherein:
one of X, Y, and Z is N; and the other two are CH or C(R);
R is H, halo, $NO_2$, $C_{1-6}$alkyl, $C_{1-6}$alkoxy, or —N($C_{0-6}$alkyl)($C_{0-6}$alkyl); and
n is 0, 1, or 2.

In one aspect, the compounds of the present invention are represented by Formula (I), wherein X is N.

In an embodiment of this one aspect, the compounds of the present invention are represented by Formula (I), wherein X is N; n is 1; and R is methyl.

In another embodiment of this one aspect, the compounds of the present invention are represented by Formula (I), wherein X is N; and n is 0.

In still another embodiment of this one aspect, the compounds of the present invention are represented by Formula (I), wherein X is N; n is 1; and R is —NH($CH_3$).

In a second aspect, the compounds of the present invention are represented by Formula (I), wherein Y is N.

In an embodiment of this second aspect, the compounds of the present invention are represented by Formula (I), wherein Y is N; n is 1; and R is methyl.

In another embodiment of this second aspect, the compounds of the present invention are represented by Formula (I), wherein Y is N; and n is 0.

In still another embodiment of this second aspect, the compounds of the present invention are represented by Formula (I), wherein Y is N; n is 1; and R is halo.

In an embodiment of this second aspect, the compounds of the present invention are represented by Formula (I), wherein Y is N; n is 1; and R is —NH($CH_3$).

In an embodiment of this second aspect, the compounds of the present invention are represented by Formula (I), wherein Y is N; n is 2; and R is methyl and halo.

In an embodiment of this second aspect, the compounds of the present invention are represented by Formula (I), wherein Y is N; n is 1; and R is $NO_2$.

In a third aspect, the compounds of the present invention are represented by Formula (I), wherein Z is N.

In an embodiment of this third aspect, the compounds of the present invention are represented by Formula (I), wherein Z is N; and n is 0.

In a fourth aspect, the compounds of the present invention are HCl salts of Formula (I), wherein X is N.

In an embodiment of this fourth aspect, the compounds of the present invention are HCl salts of Formula (I), wherein X is N; n is 1; and R is methyl.

In another embodiment of this fourth aspect, the compounds of the present invention are HCl salts of Formula (I), wherein X is N; and n is 0.

In still another embodiment of this fourth aspect, the compounds of the present invention are HCl salts of Formula (I), wherein X is N; n is 1; and R is —NH(CH$_3$).

In a fifth aspect, the compounds of the present invention are HCl salts of Formula (I), wherein Y is N.

In an embodiment of this fifth aspect, the compounds of the present invention are HCl salts of Formula (I), wherein Y is N; n is 1; and R is methyl.

In another embodiment of this fifth aspect, the compounds of the present invention are HCl salts of Formula (I), wherein Y is N; and n is 0.

In still another embodiment of this fifth aspect, the compounds of the present invention are HCl salts of Formula (I), wherein Y is N; n is 1; and R is halo.

In an embodiment of this fifth aspect, the compounds of the present invention are HCl salts of Formula (I), wherein Y is N; n is 1; and R is —NH(CH$_3$).

In an embodiment of this fifth aspect, the compounds of the present invention are HCl salts of Formula (I), wherein Y is N; n is 2; and R is methyl and halo.

In an embodiment of this fifth aspect, the compounds of the present invention are HCl salts of Formula (I), wherein Y is N; n is 1; and R is NO$_2$.

In a sixth aspect, the compounds of the present invention are HCl salts of Formula (I), wherein Z is N.

In an embodiment of this sixth aspect, the compounds of the present invention are HCl salts of Formula (I), wherein Z is N; and n is 0.

In another aspect, the compounds of the present invention may be as follows:

1.1. Formula (I), wherein X is N;
1.2. Formula (I) or 1.1, wherein Y is N,
1.3. Formula (I) or 1.1 or 1.2, wherein Z is N,
1.4. Formula (I) or any of 1.1-1.3, wherein one of X, Y, and Z is N, and the other two are C(R);
1.5. Formula (I) or any of 1.1-1.4, wherein n is 0;
1.6. Formula (I) or any of 1.1-1.4, wherein n is 1;
1.7. Formula (I) or any of 1.1-1.4, wherein n is 2;
1.8. Formula (I) or any of 1.1-1.7, wherein R is H, halo, NO$_2$, C$_{1-6}$alkyl, C$_{1-6}$alkoxy, or —N(C$_{0-6}$alkyl)(C$_{0-6}$alkyl);
1.9. Formula (I) or any of 1.1-1.8, wherein R is C$_{1-6}$alkyl (e.g., methyl);
1.10. Formula (I) or any of 1.1-1.9, wherein R is methyl;
1.11. Formula (I) or any of 1.1-1.10, wherein R is hydrogen;
1.12. Formula (I) or any of 1.1-1.11, wherein R is N(C$_{0-6}$alkyl)(C$_{0-6}$alkyl);
1.13. Formula (I) or any of 1.1-1.12, wherein R is NH(CH$_3$);
1.14. Formula (I) or any of 1.1-1.13, wherein R is halo;
1.15. Formula (I) or any of 1.1-1.14, wherein R is bromo;
1.16. Formula (I) or any of 1.1-1.14, wherein R is chloro;
1.17. Formula (I) or any of 1.1-1.14, wherein R is fluoro;
1.18. Formula (I) or any of 1.1-1.14, wherein R is iodo;
1.19. Formula (I) or any of 1.1-1.10 or 1.14-1.18, wherein R is independently methyl and/or halo (e.g., –4-methyl and –2-iodo substituted);
1.20. Formula (I) or any of 1.1-1.19, wherein R is C$_{1-6}$alkoxy;
1.21. Formula (I) or any of 1.1-1.19, wherein R is methoxy;
1.22. Formula (I) or any of 1.1-1.19, wherein R is NO$_2$;
1.23. Formula (I) or any of 1.1-1.22, wherein the chiral carbon bearing the oxy (—O—) group has an (R) absolute configuration;
1.24. Formula (I) or any of 1.1-1.22, wherein the chiral carbon bearing the oxy (—O—) group has an (S) absolute configuration;
1.25. Formula (I) or any of 1.1-1.24, wherein said compound is enantiomerically enriched with one enantiomer (e.g., wherein the absolute configuration of the chiral carbon bearing the oxy (—O—) group is predominantly (R) or predominantly (S)), for example, a compound having greater than 60% enantiomeric excess (ee), preferably greater than 75% ee, more preferably, greater than 85% ee, still more preferably, greater than 95% ee, most preferably great than 98% ee of one enantiomer;
1.26. Formula (I) or any of 1.1-1.25, wherein said compound is enantiomerically enriched with the (R) enantiomer, e.g., a compound having greater than 60% ee, more preferably greater than 75% ee, still more preferably greater than 85% ee, still more preferably, greater than 95% ee, most preferably great than 98% ee of the (R) enantiomer;
1.27. Formula (I) or any of 1.1-1.25, wherein said compound is enantiomerically enriched with the (S) enantiomer, e.g., a compound having greater than 60% ee, more preferably greater than 75% ee, still more preferably greater than 85% ee, still more preferably, greater than 95% ee, most preferably great than 98% ee of the (S) enantiomer;
1.28. Formula (I) or any of 1.1-1.27, wherein said compound is an HCl salt;
1.29. Any of the preceding formulae wherein said compounds have a K$_i$ of less than 10,000 nM, preferably less than 2,000 nM, still more preferably less than 100 nM, and most preferably less than 15 nM as described in the norepinephrine binding assay below.

Therefore, the invention is directed to a Compound of Formula (I), e.g., 1.1-1.29, in free or salt form. In a preferred embodiment, the compounds of the present invention are enriched with the (R) enantiomer. In yet another preferred embodiment, the compounds of the present invention are enriched with the (S) enantiomer. In yet another preferred embodiment, compounds of Formula (I) are selected from Examples 6, 7, 8, 12, 16 and 21, as listed in Table 1A, in free or salt form. In a particular embodiment, said compound is in hydrochloride salt form.

As used herein, the abbreviations in the specification are as follows:

"NE" refers to norepinephrine
"NET" refers to norepinephrine transporter(s).
"SERT" refers to serotonin transporter(s).
"NET/SERT" refers to norepinephrine and/or serotonin transporters.
"NRI/SRI" refers to norepinephrine/serotonin reuptake inhibitors.
"TCA" refers to tricyclic antidepressant(s).
"MAOI" refers to monoamine oxidase inhibitor(s).
"SSRI" refers to selective serotonin reuptake inhibitor(s).
"5-HT" refers to serotonin.

"VMS" refers to vasomotor symptoms.

"PET" refers to positron emission tomography.

"SPECT" refers to photon emission computed tomography.

"ee" refers to enantiomeric excess.

It is intended that when "n is 2", Compound of Formula (I) is intended to be di-substituted at the heteroaryl group and R may be independent of each other. R may also be substituted anywhere that is possible on the ring. For example, wherein X is N; n is 2 and R is methyl or halo, compounds of Formula (I) may be:

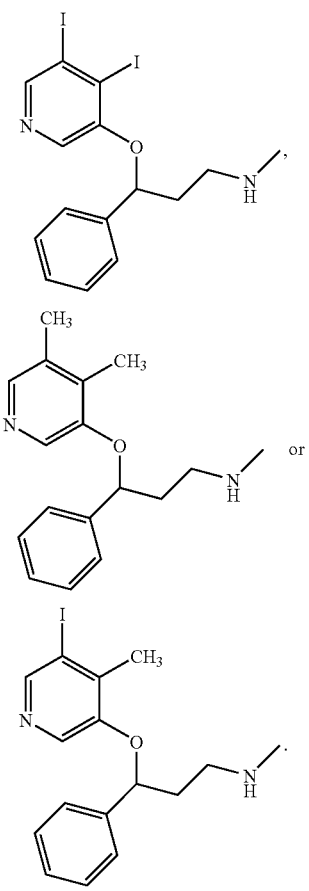

Wherein X is N; n is 2 and R is methyl and halo, compounds of Formula (I) may be, for example:

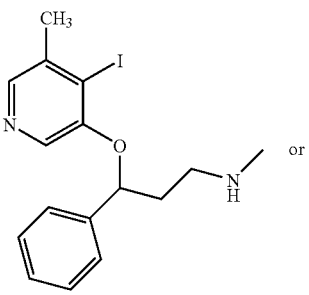

-continued

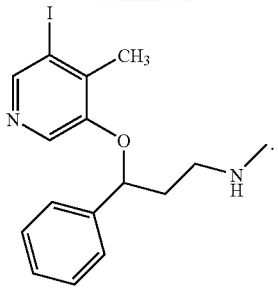

The term "alkyl" includes both straight and branched chain alkyl groups. References to individual alkyl groups such as "propyl" are specific for the straight chain version only and references to individual branched chain alkyl groups such as 'isopropyl' are specific for the branched chain version only. For example, "$C_{1-6}$alkyl" includes $C_{1-4}$alkyl, $C_{1-3}$alkyl, propyl, isopropyl and t-butyl. A similar convention applies to other radicals, for example "phenyl$C_{1-6}$alkyl" includes phenyl$C_{1-4}$alkyl, benzyl, 1-phenylethyl and 2-phenylethyl. "$C_0$alkyl" refers to a hydrogen terminus when the $C_0$alkyl is terminal and refers to a direct bond when the "$C_0$alkyl" is bridging (linking). The term "$C_{0-6}$alkyl", for example, refers to adding "$C_0$alkyl" to the scope of the "$C_{1-6}$alkyl" definition. Thus, it is understood that substituents allowed for "$C_{1-6}$alkyl" would accordingly be allowed for the "$C_{1-6}$alkyl" within the scope of "$C_{0-6}$alkyl".

The term "halo" refers to fluoro, chloro, bromo and iodo.

Where optional substituents are chosen from, for example, "1-5 independent" substituents from a list of substituents, it is to be understood that this definition includes all substituents being chosen from one of the specified groups or the substituents being chosen from two or more of the specified groups in the list. Where a substituent is recited using the molecule (parent) name, it is understood that the substituent is the radical of such molecular parent.

"$C_{1-6}$alkoxy" refers to —O—$C_{1-6}$alkyl. Examples of "$C_{1-6}$alkoxy" include methoxy, ethoxy and propoxy.

Examples of "—($C_{0-6}$alkyl)-N($C_{0-6}$alkyl)($C_{0-6}$alkyl)" include methylamino, ethylamino, di-N-methylamino, di-(N-ethyl)amino, and N-ethyl-N-methylamino.

A salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid which affords a physiologically-acceptable cation, for example a salt with methylamine, dimethylamine, trimethylamine, piperidine, morpholine or tris-(2-hydroxyethyl)amine. In addition a salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention, are therefore also included. Consequently, the present invention encompasses novel Compounds of Formula (I) in free or salt form, including salts that are suitable as well as salts which are unsuitable for pharmaceutical.

It is also to be understood that certain compounds of the formula (I) can exist in solvated as well as unsolvated forms such as, for example, hydrated forms. It is to be understood that the invention encompasses all such solvated forms which possess NET regulatory activity.

Further, it is understood that the compounds of formula (I) can exist in various stereoisomeric forms and in mixtures of such forms. The present invention encompasses all such forms and mixtures of such forms, enantiomers and chiral. The term "enantiomeric", "enantiomerically enriched" or "enantiomerically pure" form as used in this invention means substantially enriched with one enantiomer, wherein the absolute configuration of the chiral carbon bearing the oxy (—O—) group is predominantly (R) or predominantly (S), for example, a compound having greater than 60% enantiomeric excess (ee), preferably greater than 75% ee, more preferably, greater than 85% ee, still more preferably, greater than 95% ee, most preferably great than 98% ee of either the (R) or the (S) enantiomer. The term "enantiomeric excess" is a well known term and may be determined by one skilled in the art.

The chiral carbon bearing the oxy (—O—) group having an (R) or (S) absolute configuration refers to the following configurations:

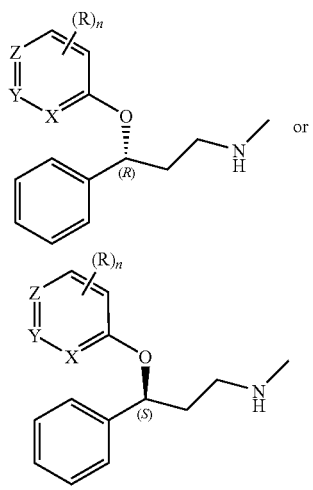

Particular values of variable groups are as follows. Such values may be used where appropriate with any of the definitions, claims or embodiments defined hereinbefore or hereinafter.

In another aspect, the present invention comprises any of the following compounds, represented by Formula (I) above, with the variables as identified:

TABLE 1A

| Example | X | Y | Z | R |
|---|---|---|---|---|
| 1 | N | C | C | 4-Me |
| 2 | C | N | C | 6-Me |
| 3 | C | N | C | H |
| 4 | N | C | C | H |
| 5 | C | C | N | H |
| 6 | C | N | C | 2-Br |
| 7 | C | N | C | 2-NHMe |
| 8 | C | N | C | 2-Cl |

TABLE 1A-continued

| Example | X | Y | Z | R |
|---|---|---|---|---|
| 9 | C | N | C | 2-Me |
| 10 | C | N | C | 2-NHMe |
| 11 | C | N | C | 3-Cl |
| 12 | C | N | C | 4-Me, 2-I |
| 13 | N | C | C | 3-NHMe |
| 14 | C | N | C | 2-NO$_2$ |
| 15 | C | N | C | 2-F |
| 16 | C | N | C | 2-I |
| 17 | C | N | C | 4-Me |
| 18 | C | N | C | 5-Cl |
| 19 | C | N | C | 2-F |
| 20 | C | N | C | 2F, 4-Me |
| 21 | C | N | C | 2-OMe | in free or salt form.

In a preferred embodiment, the Compounds of Formula (I) is selected from Examples 6, 7, 8, 12, 16 and 21, as listed in Table 1A, in free or salt form. In another preferred embodiment, Examples 6, 7, 8, 12, 16 and 21, are enriched with the (R) enantiomer. In yet another preferred embodiment, Examples 6, 7, 8, 12, 16 and 21, are enriched with the (S) enantiomer. In an especially preferred embodiment, the Compounds of Formula (I) are selected from Example 6(R), 6(S), 12, 12(R), 16(R), 16(S) and 21 as listed in Table 1B, in free or salt form. In yet another preferred embodiment, compounds of formula (I) is in hydrochloric salt form.

According to a further aspect of the invention there is provided a pharmaceutical composition which comprises a compound of the formula (I), e.g., any of formulae 1.1-1.29 in free or a pharmaceutically acceptable salt thereof, as defined hereinbefore, in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general, the above compositions may be prepared in a conventional manner using conventional excipients.

The compound of formula (I) e.g., any of formulae 1.1-1.29 in free or salt form will normally be administered to a warm-blooded animal at a unit dose within the range 1-1000 mg/kg, and this normally provides a therapeutically effective dose. Preferably a daily dose in the range of 5-100 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention, there is provided a compound of the formula (I), e.g., any of formulae 1.1-1.29 in free or pharmaceutically acceptable salt thereof, for use in a method of treatment of the human or animal body by therapy.

We have found that the compounds defined in the present invention, or a pharmaceutically acceptable salt thereof, can penetrate the blood-brain barrier and regulate NET and/or SERT. Accordingly, the compounds of the present invention are useful in the treatment of NET/SERT mediated conditions, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, fibromyalgia, and naturally, surgically or medically-induced menopausal symptoms such as vasomotor symptoms, e.g., hot flashes, especially anxiety, depression and vasomotor symptoms. Therefore, the invention provides a method of treating a disease or condition mediated by NET and/or SERT comprising administering an effective amount of a compound of formula (I), e.g., any of formulae 1.1-1.29, in free or pharmaceutically acceptable salt form, to a patient in need thereof. In a particular embodiment, the invention provides a method of treating a disease or condition mediated by NET and/or SERT as described herein, wherein said disease or condition is anxiety or depression. In another particular embodiment, the invention provides a method of treating a disease or condition mediated by NET and/or SERT as described herein, wherein said disease or condition is vasomotor symptoms, e.g., hot flashes.

Thus according to this aspect of the invention, there is provided a compound of the formula (I), e.g., any of formulae 1.1-1.29, in free or a pharmaceutically acceptable salt thereof, as defined hereinbefore for use as a medicament.

According to a further aspect of the invention, there is provided the use of a compound of the formula (I), e.g., any of formulae 1.1-1.29, in free or a pharmaceutically acceptable salt thereof, as defined hereinbefore in the manufacture of a medicament for use in the regulation of NET/SERT in a warm-blooded animal such as man.

According to an aspect of the invention, there is provided the use of a compound of the formula (I), e.g., any of formulae 1.1-1.29, in free or a pharmaceutically acceptable salt thereof, as defined hereinbefore in the manufacture of a medicament for use in the production of an NET/SERT regulator across the blood-brain barrier in a warm-blooded animal such as man.

According to a further feature of the invention, there is provided the use of a compound of the formula (I), e.g., 1.1-1.29, in free or salt form, as defined herein before in the manufacture of a medicament for use in the treatment of NET/SERT mediated conditions, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, fibromyalgia and naturally, surgically or medically-induced menopausal or andropausal symptoms such as vasomotor symptoms, e.g., hot flashes, especially anxiety, depression and vasomotor symptoms, e.g., hot flashes. In a preferred embodiment, the invention provides use of a compound of the formula (I), e.g., any of formulae 1.1-1.29, in free or a pharmaceutically acceptable salt form, in the manufacture of a medicament for the treatment of anxiety or depression. In another preferred embodiment, the invention provides use of a compound of the formula (I), e.g., any of formulae 1.1-1.29, in free or a pharmaceutically acceptable salt form, in the manufacture of a medicament for the treatment of vasomotor symptoms, e.g., hot flashes.

According to a further feature of this aspect of the invention, there is provided a method for producing a regulatory effect on NET in a warm-blooded animal, such as man, in need of such NET/SERT regulating which comprises administering to said animal an effective amount of a compound of formula (I), e.g., any of formulae 1.1-1.29, in free or a pharmaceutically acceptable salt thereof.

Furthermore, the compounds of this invention are useful in the treatment, control and management of diseases characterized by malregulation of NET/SERT, especially in the brain—for example, depression. Accordingly, the present invention provides methods of treatment of NET/SERT mediated conditions, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, fibromyalgia and naturally, surgically or medically-induced menopausal or andropausal symptoms such as vasomotor symptoms, e.g., hot flashes, especially anxiety, depression and vasomotor symptoms or hotflashes. The methods of treatment of NET/SERT mediated conditions comprise administering to a patient in need thereof an effective amount of a compound of formula (I), e.g., any of formulae 1.1-1.29, in free or pharmaceutically acceptable salt form.

The present invention also provides methods of treatment of disease characterized by dysfunctional regulation of NET/SERT, comprising the administration of an effective amount of a compound or composition of the present invention in free or salt form to a human or animal patient in need thereof.

In a further aspect of the invention there is provided a pharmaceutical composition which comprises a compound of the formula (I), e.g., any of formulae 1.1-1.29, in free or a pharmaceutically acceptable salt form, as defined herein before in association with a pharmaceutically-acceptable diluent or carrier for use in the treatment, control and management of diseases characterized by malregulation of NET/SERT. In a particular embodiment, the invention provides a pharmaceutical composition which comprises a compound of formula (I), in free or a pharmaceutically acceptable salt thereof, e.g., 1.1-1.29, in admixture with a pharmaceutically acceptable diluent or carrier for use in the treatment, control and management of diseases characterized by malregulation of NET/SERT in the brain.

In a further aspect of the invention, there is provided a pharmaceutical composition which comprises a compound of the formula (I), e.g., any of formulae 1.1-1.29, in free or a pharmaceutically acceptable salt thereof, as defined herein before in association with a pharmaceutically-acceptable diluent or carrier for use in the treatment of NET/SERT mediated conditions, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, fibromyalgia and naturally, surgically or medically-induced menopausal or andropausal symptoms such as vasomotor symptoms, e.g., hot flashes, especially anxiety and depression and vasomotor symptoms, e.g., hot flashes.

The treatment methods include administering the compounds of the present invention, in free or salt form, together with other therapeutic compounds to treat NET/SERT mediated conditions as hereinbefore described, e.g., depression. Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to a further feature of the invention, there is provided a method for treating, alleviating, preventing or controlling vasomotor symptoms, e.g., hot flashes, comprising administering to a subject in need thereof, a therapeutically effective amount of at least one compound of Formula (I), e.g., any of formulae 1.1-1.29, in free or pharmaceutically acceptable salt form as defined herein before and optionally in association with a pharmaceutically-acceptable diluent or carrier.

The term "vasomotor symptoms" include, but are not limited to hot flashes (flushes), insomnia, sleep disturbances, mood disorders, irritability, excessive perspiration, night sweats, fatigue and other similar symptoms caused by thermoregulatory dysfunction. The term "hot flash" refers to an episodic disturbance of the body temperature leading to symptoms ranging from a warming sensation, intense heat on the upper body and face, redness, perspiration and sometimes followed by chills. The term hot flashes may be used interchangeably with vasomotor symptoms.

The treatment methods for vasomotor symptoms include administering the compounds of the present invention, in free or salt form, e.g., Compound of Formula (I) or any of formulae 1.1-1.29, in free or pharmaceutically acceptable salt form, together with other therapeutic compounds to treat NET/SERT mediated conditions as hereinbefore described. Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

A "therapeutically effective amount" refers to an amount of compounds (e.g., Compounds of Formula (I)) or compositions at specific dosages and for a specific amount of time, sufficient to treat a disease or condition, e.g., NET/SERT mediated conditions, e.g., dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, fibromyalgia and naturally, surgically or medically-induced menopausal or andropausal symptoms such as vasomotor symptoms, e.g., hot flashes especially anxiety, depression and vasomotor symptoms, e.g., hot flashes. Wherein the therapeutic effective amount refers to a weight amount of the compounds of the invention, the weight amount is based on the compounds in free base form unless otherwise indicated.

In another embodiment, the invention provides use of a compound of formula (I), e.g., any of formulae 1.1-1.29, in free or salt form, in the manufacture of a medicament for treating any disease or condition characterized by naturally, surgically or medically-induced menopausal or andropausal symptoms such as vasomotor symptoms, e.g., hot flashes. In a further embodiment, the invention provides use of a compound of formula (I), e.g., any of formulae 1.1-1.29, in free or salt form, in the manufacture of a medicament for treating vasomotor symptoms, e.g., hot flashes.

In another embodiment, the invention provides a method for treating, alleviating, preventing or controlling vasomotor symptoms comprising (a) administering to a subject in need thereof a therapeutically affective amount of a compound of Formula (I), e.g., any of formulae 1.1-1.29, in free or pharmaceutically acceptable salt form, as hereinbefore described, and (b) further administering sequentially or simultaneously, at least one other adrenergic$_{\alpha 2}$ receptor antagonist.

The adrenergic$_{\alpha 2}$ receptor antagonists useful for the present invention include, but not limited to, atipamezole, 2-[2-(4-(2-methoxyphenyl)piperazin-1-yl) ethyl]-4,4-dimethyl-1,3-(2H, 4H)-isoquinolindione dihydrochloride (ARC 239 dihydrochloride), 2-[(4,5-dihydro-1H-imidazol-2-yl) methyl]-2,3-dihydro-1-methyl-1H-isoindole maleate (BRL 44408 maleat), BRL48962, BRL41992, SKF 104856, SKF 104078, MK912, 2-(2-ethyl-2,3-dihydro-2-benzofuranyl)-4,5-dihydro-1H-imidazole hydrochloride (efaroxan hydrochloride), 2-(1,4-benzodioxan-2-yl)-2-imidazoline hydrochloride (idazoxan hydrochloride), 2-(1-ethyl-2-indazoyl) methyl-1,4-benzodioxan hydrochloride (imiloxan hydrochloride), 17α -hydroxy-20α -yohimban-16β-carboxylic acid, methyl ester hydrochloride (rauwolscine hydrochloride), (8aR,12aS,13aS)-5,8,8a,9,10,11,12,12a,13,13a-dechydro-3-methoxy-12-(ethylsulfonyl)-6H-isoquino[2,1-y][1,6]naphthyridine hydrochloride (RS 79948 hydrochloride), 2-(2,3-dihydro-2-methoxy-1,4-benzodioxin-2-yl)-4,5-dihydro-1H-imidazole hydrochloride (RX 821002 hydrochloride), 8-[(2,3-dihydro-1,4-benzodioxin-2-yl)methyl]-1-phenyl-1,3,8-triazaspiro[4,5]decan-4-one (spiroxatrine), 17a-hydroxyyohimban-16a-carboxylic acid methyl ester hydrochloride (yohimbine hydrochloride), 2-[(2,3-dihydro-1,4-benzodioxin-2-yl)methyl]-1-ethyl-1H-imidazole, and combinations and pharmaceutically acceptable salts thereof.

In a further embodiment, said adrenergic$_{\alpha 2}$ receptor antagonist is an adrenergic$_{\alpha 2B}$ receptor antagonist selected from a group consisting of 2-(1-ethyl-2-imidazoyl)methyl-1,4-benzodioxan (imiloxan), 2-[(2,3-dihydro-1,4-benzodioxin-2-yl)methyl]-1-ethyl-1H-imidazole, 2-[2-[4-(2-methoxyphenyl)-1-piperazinyl]ethyl]-4,4-dimethyl-1,3 (2H, 4H)-isoquinolinedione (ARC 239), or a combination or a pharmaceutical salt thereof.

In addition to their use in therapeutic medicine, the compounds of formula (I), e.g., any of formulae 1.1-1.29, in free or pharmaceutically acceptable salt forms are also useful as pharmacological tools in the development and standardisation of in vitro and in vivo test systems for the evaluation of the effects of regulation of NET and/or SERT, especially in the brain, as part of the search for new therapeutic agents.

The term "NET/SERT mediated conditions" or "NET and/or SERT mediated conditions" or "disease characterized by malregulation of NET/SERT" referred herein include but are not limited to one or more of the follow diseases or conditions: dysphoria, depression (including major depressive disorder, dysthymia, adjustment disorder with depressed mood, and depression associated with bipolar disorder), anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, fibromyalgia and vasomotor symptoms, e.g., hot flashes. Therefore, the methods of the invention encompass methods of treating these diseases. In a preferred embodiment, the disease or condition of the methods of the invention is depression or anxiety. In another preferred embodiment the disease or condition of the method of the invention is vasomotor symptoms, e.g., hot flashes.

The term "subject" includes a warm-blooded animal, including the human species and intends to include both the male or female gender unless otherwise indicated. The subject according to the current invention for the treatment of vasomotor symptoms, e.g., hot flashes includes not only women of advanced age who have gone through menopause (postmenopausal), but also pre- or peri-menopausal female wherein menopause may be naturally, chemically and/or surgically induced (e.g., those who have undergone oophorectomy, hysterectomy, chemotherapy, radiation of the pelvis or those who have suppressed estrogen production such as those who have undergone long-term use of corticosteroids or suffer from Cushing's syndrome or gonadal dysgenesis). The term subject according to the current invention for the treatment of vasomotor symptoms, e.g., hot flashes also includes andropausal male.

The term "pre-menopausal" or "premature menopause" means before the menopause. Both "premature menopause" and "artificial menopause" may refer to menopause that occurs as a result of, e.g., ovarian failure of unknown cause that may occur before age of 40. It may also be associated with smoking, living at high altitude, or poor nutritional status. Artificial menopause may result from oophorectomy, chemotherapy, radiation of the pelvis, or any process that impairs ovarian blood supply.

The term "peri-menopausal" means during the menopause.
The term "post-menopausal" means after the menopause.
The term "andropause" refers to condition or disorder characterized by symptoms, including, but not limited to reduction in Leydig cell numbers and a decline in androgen production, occurring in men, generally after middle age. Andropausal men therefore may also experience symptoms including, but not limited to fatigue, insomnia, hot flushes, and sweating. Accordingly, the current invention also anticipates use of the compounds of the present invention by naturally, chemically and/or surgically induced andropausal male.

In the above other pharmaceutical composition, process, method, use and medicament manufacture features, the alternative and preferred embodiments of the compounds of the invention described herein also apply.

EXAMPLES

The invention will now be illustrated by the following non limiting examples in which, unless stated otherwise:
(i) temperatures are given in degrees Celsius (° C.); operations were carried out at room or ambient temperature ("rt") were at a temperature in the range of 18-25° C.;
(ii) organic solutions were dried over anhydrous sodium sulphate; evaporation of solvent is carried out using a rotary evaporator under reduced pressure (600-4000 Pascals; 4.5-30 mmHg) with a bath temperature of up to 60° C.;
(iii) in general, the course of reactions is followed by TLC and reaction times are given for illustration only;
(iv) final products had satisfactory proton nuclear magnetic resonance (NMR) spectra and/or mass spectral data;
(v) yields are given for illustration only and are not necessarily those which can be obtained by diligent process development; preparations were repeated if more material is required;
(vii) when given, NMR data is in the form of delta values for major diagnostic protons, given in parts per million (ppm) relative to tetramethylsilane (TMS) as an internal standard, determined at 400 MHz using perdeuterio dimethyl sulphoxide (DMSO-$d_6$) as solvent unless otherwise indicated;
(vii) chemical symbols have their usual meanings; International System units and symbols are used;
(viii) solvent ratios are given in volume:volume (v/v) terms; and
(ix) mass spectra were run with an electron energy of 70 electron volts in the chemical ionization (CI) mode using a direct exposure probe; where indicated ionization is effected by electron impact (EI), fast atom bombardment (FAB) or electrospray (ESP); values for m/z are given; generally, only ions which indicate the parent mass are reported; and unless otherwise stated, the mass ion quoted is $[MH]^+$;
(x) where a synthesis is described as being analogous to that described in a previous example the amounts used are the millimolar ratio equivalents to those used in the previous example;
(xi) the following abbreviations have been used:

| | |
|---|---|
| $Cs_2CO_3$ | cesium carbonate; |
| HOBt | 1H-benzo[d][1,2,3]triazol-1-ol; |
| HPLC | high performance liquid chromatography; |
| MeOH | methanol; |
| $NaHCO_3$ | sodium bicarbonate; |
| BOP | benzotriazol-1-yloxytris(dimethylamino)phosphonium hexafluorophosphate; |
| THF | tetrahydrofuran; |
| DMF | N,N-dimethylformamide; |
| EtOAc | ethyl acetate; |
| DIEA | N, N-diisopropylethylamine; |
| DCM | dichloromethane; |
| DMSO | dimethylsulphoxide; |
| Me | Methyl; |
| MeCN | acetonitrile; and |

(xii) "ISCO" refers to normal phase flash column chromatography using 12 g and 40 g pre-packed silica gel cartridges used according to the manufacturer's instructions obtained from ISCO, Inc, (Lincoln, Nebr., U.S.A.).

Biology

The NET binding was assayed to determine if the compounds specifically bind to NET in the rat forebrain. Forebrain tissue has a moderate density of NET and can be accurately separated from other brain structures. Rat forebrain was obtained fresh from Sprague-Dawley rat brains (Taconic Farm, N.Y., U.S.A.). Tissue was homogenized in 30 volumes of buffer (50 mM Tris-HCl, pH 7.4 containing 120 mM NaCl and 5 mM KCl). The homogenates were centrifuged at 10,000 rpm for 15 min. The resulting pellets re-suspended and re-centrifuged and the procedure repeated once more. Binding experiments were performed in 7 mL glass tubes with a final volume of 1.0 mL/tube. For inhibition constant determinations, aliquots of membrane suspensions (equivalent to 3 mg wt per tube) were mixed with buffer and 1 nM [$^3$H]nisoxetine. In addition, unlabeled test NET ligands in concentrations ranging from $10^{-3}$ to $10^{-12}$ (micro- to pico-molar) were added. Incubation was carried out for 60 min at rt and then the study terminated by separation of bound from free radioligand by filtration through glass fiber filters presoaked with 1% polyethylenimine. The filters were processed and assayed for radioactivity using a scintillation counter. A plot of average counted per minute (CMP, n=3) versus test ligand concentration was made, and Prism (3.0cx, GraphPad) was used to determine compound inhibition constant ($IC_{50}$) and binding affinity ($K_i$).

The method was validated by running ten assays performed assessing the binding of nisoxetine to NET using membranes prepared as above. The $K_D$ of nisoxetine under these conditions was determined to be 1.29±0.23 nM (n=6) thus, validating the assay.

The compounds of the present invention resulted in binding affinities ranging from 100,000 nM to less than 3 nM when tested in HCl salt form. It is advantageous that the binding affinity be less than 10,000 nM, even more advantageously less than 2,000 nM, and still more advantageously less than 100 nM, and most advantageously less than 15 nM.

The compounds of the invention also inhibit serotonin transporter activity, with selected compounds having an $IC_{50}$ of ca. $5 \times 10^{-8}$ M or lower.

The binding affinity (Ki) for human norepinephrine transporter may also be measured using a radio-labelled binding assay wherein the compounds of the present invention are tested in recombinant/CHO cells in the presence of [3H]-nisoxetine as ligand and desipramine as non-specific reference compounds. Similarly, cellular assay may be used wherein the compounds of the present invention are tested in SH-SY-5Y cells in the presence of [3H]-norepinephrine as ligand and protriptyline as non-specific reference compounds. In both methods, various compounds of the present invention show a binding affinity of less than 500 nM, in particular instances about 500-50 nM.

Examples

EXAMPLES were made following the reaction route outlined in Scheme 1 below to make the free base and the HCl salt:

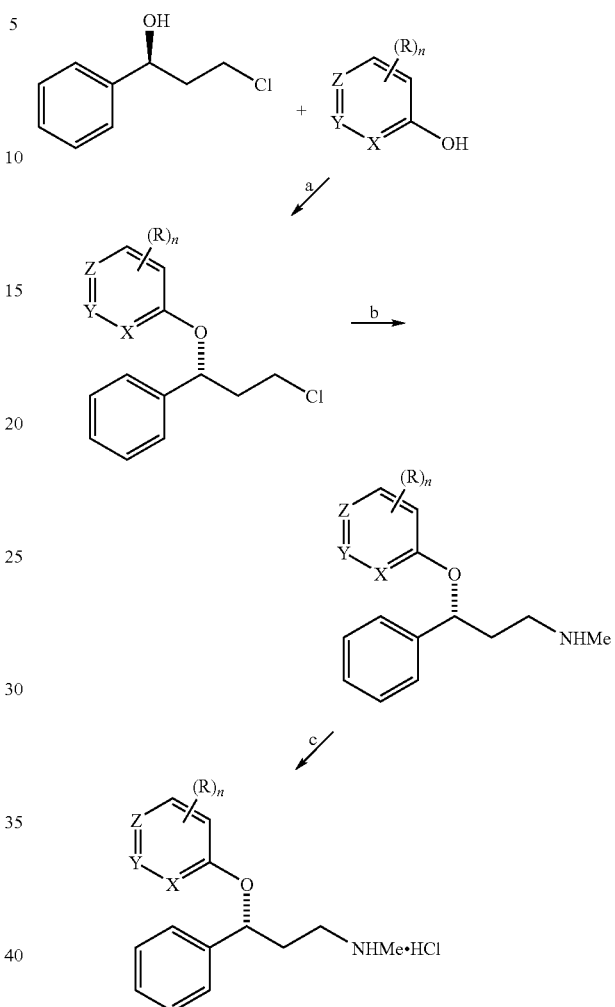

The conditions and reagents for the steps are as follows: (a) DIAD, TPP, THF, 0° C.; (b) 40% aqueous $CH_3NH_2$, NaI, 80° C., 2 h; (c) 2N HCl in EtOAc.

For a particular stereoconformation, the following specific embodiment of Scheme 1 can be used as an example:

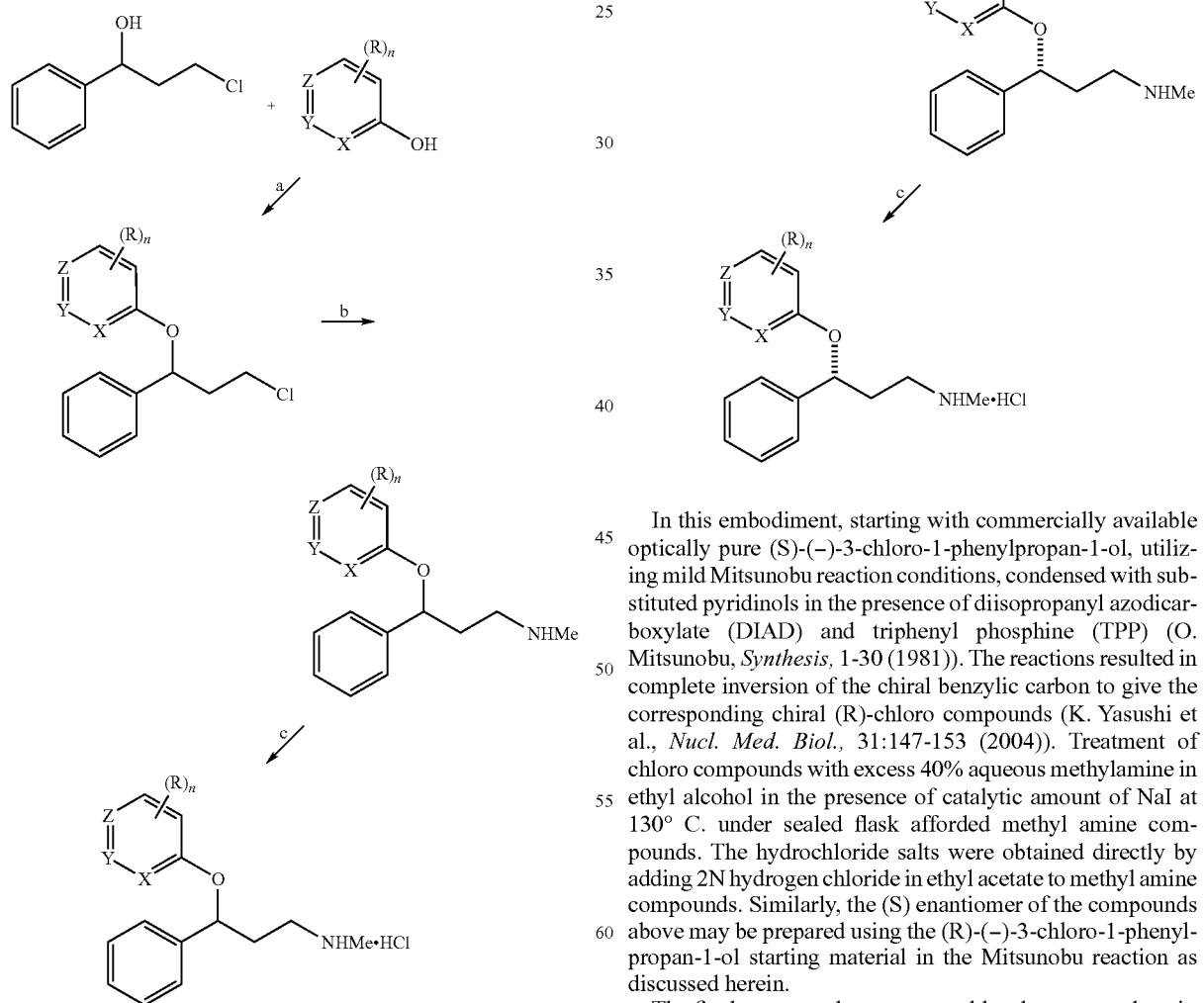

In this embodiment, starting with commercially available optically pure (S)-(−)-3-chloro-1-phenylpropan-1-ol, utilizing mild Mitsunobu reaction conditions, condensed with substituted pyridinols in the presence of diisopropanyl azodicarboxylate (DIAD) and triphenyl phosphine (TPP) (O. Mitsunobu, *Synthesis*, 1-30 (1981)). The reactions resulted in complete inversion of the chiral benzylic carbon to give the corresponding chiral (R)-chloro compounds (K. Yasushi et al., *Nucl. Med. Biol.*, 31:147-153 (2004)). Treatment of chloro compounds with excess 40% aqueous methylamine in ethyl alcohol in the presence of catalytic amount of NaI at 130° C. under sealed flask afforded methyl amine compounds. The hydrochloride salts were obtained directly by adding 2N hydrogen chloride in ethyl acetate to methyl amine compounds. Similarly, the (S) enantiomer of the compounds above may be prepared using the (R)-(−)-3-chloro-1-phenylpropan-1-ol starting material in the Mitsunobu reaction as discussed herein.

The final compounds were not stable when exposed to air, especially when the sample is dissolved in solution, so the pure products were kept in freezer under nitrogen. All the compounds were confirmed by $^{1}HNMR$, LC-MS and $^{13}CNMR$. The data of EXAMPLE 6 (R)-(−)-NM-methyl-3-

(2-bromo-3-pyridinoxy)-3-phenylpropanamine were, for example, LC-MS, EI (m/z): 321 (100%, M$^+$), 323 (98%, (M+2)$^+$). $^1$HNMR (CD$_{30}$D), 400 Mhz), δ(ppm): 7.95 (dd, J=4.2, 1.8 Hz, 1H), 7.49 (m, 5H), 7.25 (m, 2H), 5.66 (dd, J=4.0, 8.5 Hz, 1H), 3.32 (m, 2H), 2.82 (s, 3H), 2.49 (m, 1H), 2.38 (m, 1H). $^{13}$C NMR (CDCl$_3$, 100 MHz), δ(ppm): 151.18, 145.85, 139.88, 133.08, 131.34, 131.06, 128.86, 126.41, 126.14, 83.01, 51.01, 39.13, 33.82.

The EXAMPLES are listed below in Table 18:

TABLE 1B

| Ex. | X | Y | Z | R |
|---|---|---|---|---|
| 1 | N | C | C | 4-Me |
| 2 | C | N | C | 6-Me |
| 3 | C | N | C | H |
| 4 | N | C | C | H |
| 5 | C | C | N | H |
| 6 | C | N | C | 2-Br |
| 7 | C | N | C | 2-NHMe |
| 8 (R-) | C | N | C | 2-Cl |
| 9 | C | N | C | 2-Me |
| 8 (S-) | C | N | C | 2-Cl |
| 10 | C | N | C | 2-NHMe |
| 6 (S-) | C | N | C | 2-Br |
| 11 | C | N | C | 3-Cl |
| 12 | C | N | C | 4-Me, 2-I |
| 12 (R) | C | N | C | 4-Me, 2-I |
| 13 | N | C | C | 3-NHMe |
| 6 (R-) | C | N | C | 2-Br |
| 14 | C | N | C | 2-NO$_2$ |
| 15 | C | N | C | 2-F |
| 16 (S-) | C | N | C | 2-I |
| 16 (R) | C | N | C | 2-I |
| 14 (S-) | C | N | C | 2-NO$_2$ |
| 17 | C | N | C | 4-Me |
| 18 | C | N | C | 5-Cl |
| 19 | C | N | C | 2-F |
| 20 | C | N | C | 2F, 4-Me |
| 21 | C | N | C | 2-OMe |

Effects of the Compounds of the Invention on Vasomotor Symptoms

Overiectomized Rat Model: The effectiveness of the compounds of the present invention to reduce hot flashes may be evaluated according to the procedure provided in Maswood et. al., *Neuroendocrinology* 84:330-338 (2006). Ovariectomized female rats are housed on a 12-hour light/dark cycle. A telemetric transmitter is implanted in the dorsal scapular region of the rat and tip of the tunnel probe is inserted 2.5 cm beyond the base of the tail to measure the tail skin temperature (TST). For measurement of the core body temperature (CBT), a 3-4 cm long incision is made in the midline of the abdomen of the rats through the abdominal musculature and a transmitter is placed in the abdominal cavity. A vehicle is administered subcutaneously to the rat 0.5 h before the onset of the dark phase and TST is monitored continuously for 12 hours to establish the baseline. Twenty-four hours later, either vehicle or test compounds of the present invention are administered subcutaneously. TST is monitored for 12 hours. An average temperature is calculated for every 30-min time point. The change in temperature is calculated by taking the average temperature for each 30-min time point on the compound dosing day minus the overall average baseline temperature on vehicle dosing day (average temperature over 12 hours).

Morphine-dependent Rat Model: The effectiveness of the compounds of the present invention to reduce hot flashes is evaluated by measuring its ability to reduce morphine-induced rise in TST. Ovariectomized rats are subcutaneously injected with a vehicle (sterile water) once daily for 8 days. On day-4, two tablets of slow-release morphine are implanted subcutaneously in the dorsal scapular region of the rats to induce morphine dependence. On day-5 and -6, morphine withdrawal is induced by subcutaneous administration of 1.0 mg/Kg of naloxone, a general opioid antagonist. Compounds of the present invention or combinations thereof are administered (1.0, 5, 10, 20, 40 mg/Kg) to the rats 1 hour before naloxone injection. Ketamine (40 mg/Kg) is injected after test compound to induce sedation so as to avoid temperature fluctuation due to stress associated with restriction of their movement and attachment of thermistor probe to the their tails. All drug-related effects are compared to a vehicle control group which also receives ketamine. TST is monitored continuously for 35 minutes. The average TST measured 25, 30 and 35 minutes prior to naloxone injection is used to establish a baseline temperature. Hot flash reduction is determined by evaluating the statistical differences between the baseline temperature and 15 minutes after naloxone treatment when the change in TST is observed to be maximum.

Using the morphine-dependent rat model, the results will indicate that the compounds of the present invention abate naloxone-induced flush.

What is claimed is:

1. A compound of formula (I):

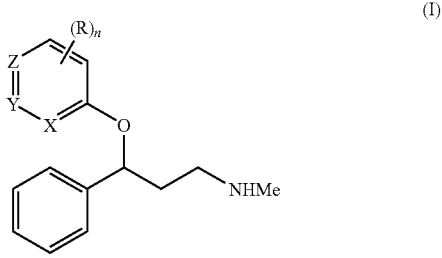

in free or salt form, wherein:
one of X, Y, and Z is N; and the other two are CH or C(R):
R is H, halo, NO$_2$, C$_{1-6}$alkyl, C$_{1-6}$alkoxy, or —N(C$_{0-6}$alkyl)(C$_{0-6}$alkyl); and
n is 0, 1, or 2.

2. The compound according to claim 1, selected from a group consisting of the following:

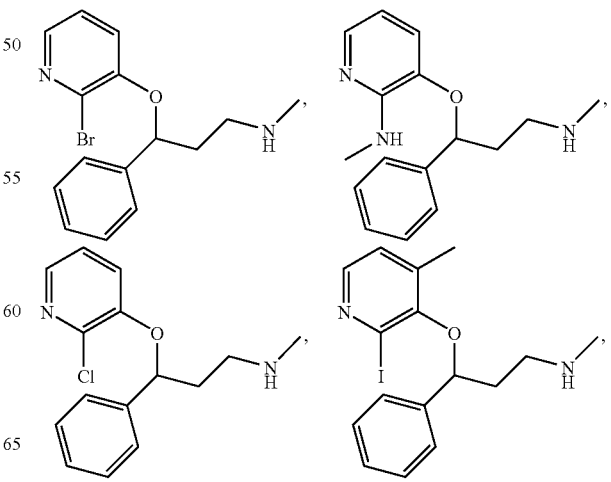

-continued

[Structure: 2-iodopyridine-oxy compound with phenyl and NHMe chain]

and

[Structure: 2-methoxypyridine-oxy compound with phenyl and NHMe chain]

in free or salt form.

3. The compound according to claim 1, wherein said compound is enriched with the (R) enantiomer in greater than 60% enantiomeric excess.

4. The compound according to claim 1, wherein said compound is enriched with the (S) enantiomer in greater than 60% enantiomeric excess.

5. The compound according to claim 1, wherein said salt form comprises a hydrochloride salt.

6. A method of modulating NET/SERT comprising administering an effective amount of the compound according to claim 1, in a free or pharmaceutically acceptable salt form.

7. A method of inhibiting NET/SERT comprising administering an effective amount of the compound according to claim 1, in a free or pharmaceutically acceptable salt form.

8. A method of treating a disease or disorder mediated by NET/SERT comprising administering an effective amount of a compound of formula (I) according to claim 1:

[Structure of Formula (I) showing Z-Y-X ring with $(R)_n$ substituent, O linker, phenyl, and NHMe chain]

(I)

in free or pharmaceutically acceptable salt form, wherein:
one of X, Y, and Z is N; and the other two are CH or C(R);
R is H, halo, $NO_2$, $C_{1-6}$alkyl, $C_{1-6}$alkoxy, or —N($C_{0-6}$alkyl)($C_{0-6}$alkyl); and
n is 0, 1, or 2,
to a patient in need thereof.

9. The method according to claim 8, wherein the compound of Formula (I) is selected from a group consisting of

[Five structures shown: 2-bromo-, 2-methylamino-, 2-chloro-, and 2-iodo-4-methyl pyridine-oxy compounds; and additional 3-iodo and 2-methoxy pyridine-oxy compounds]

and in free or pharmaceutically acceptable salt form.

10. The method according to claim 8, wherein said compound is enriched with the (S) enantiomer in greater than 60% enantiomeric excess.

11. The method according to claim 8, wherein said compound is enriched with the (R) enantiomer in greater than 60% enantiomeric excess.

12. The method according to claim 8, wherein the disease or condition mediated by NET and/or SERT is selected from a group consisting of dysphoria, depression, anxiety, sleep disorders, gastric motility disorders, sexual dysfunction, brain trauma, memory loss, appetite disorders, bulimia, obesity, substance abuse, alcoholism, tobacco addiction, obsessive-compulsive disease, panic disorder, premenstrual syndrome, migraine, bipolar disorders, fibromyalgia, and vasomotor symptoms or hot flashes.

13. The method according to claim 8, wherein the disease or condition is depression.

14. The method according to claim 8, wherein the disease or condition is anxiety.

15. The method according to claim 8, wherein the disease or condition is vasomotor symptoms or hot flashes.

16. The method according to claim 8, wherein the compound according to claim 1 is in hydrochloride salt form.

17. A pharmaceutical composition which comprises a compound of Formula I according to claim 1, in free or a pharmaceutically acceptable salt form, in association with a pharmaceutically-acceptable diluent or carrier.

* * * * *